(12) United States Patent
Shim et al.

(10) Patent No.: US 7,759,285 B2
(45) Date of Patent: Jul. 20, 2010

(54) ABSORBENT FOR SEPARATION OF CARBON DIOXIDE

(75) Inventors: Jae Goo Shim, Daejeon (KR); Jun Han Kim, Daejeon (KR); Kyung Ryong Jang, Daejeon (KR); Chung Kul Ryu, Daejeon (KR); Hee Moon Eum, Daejeon (KR); Hyun Soo Lim, Daejeon (KR)

(73) Assignee: Korea Electric Power Corporation (KR)

( * ) Notice: Subject to any disclaimer, the term of this patent is extended or adjusted under 35 U.S.C. 154(b) by 510 days.

(21) Appl. No.: 11/616,561

(22) Filed: Dec. 27, 2006

(65) Prior Publication Data

US 2008/0125314 A1 May 29, 2008

(30) Foreign Application Priority Data

Nov. 29, 2006 (KR) .................. 10-2006-0119336

(51) Int. Cl.
*B01J 20/22* (2006.01)
*C07C 229/06* (2006.01)
*B01D 53/14* (2006.01)
*B01D 53/62* (2006.01)

(52) U.S. Cl. .................. 502/401; 562/553; 423/226; 423/228

(58) Field of Classification Search .......... 502/401; 562/553; 423/226, 228, 229, 232
See application file for complete search history.

(56) References Cited

U.S. PATENT DOCUMENTS

| 3,042,483 A | * | 7/1962 | Wolfram et al. ........ 423/437.1 |
| 3,642,430 A | * | 2/1972 | Benson et al. ........... 423/223 |
| 4,094,957 A | * | 6/1978 | Sartori et al. ............ 423/223 |
| 5,744,110 A | * | 4/1998 | Mimura et al. .......... 423/226 |
| 2006/0104877 A1 | * | 5/2006 | Cadours et al. ......... 423/226 |

FOREIGN PATENT DOCUMENTS

| DE | 2605618 | * | 8/1977 |
| JP | 61-101244 | * | 5/1986 |

OTHER PUBLICATIONS

Hook, "An Investigation of Some Sterically Hindered Amines as Potential Carbon Dioxide Scrubbing Compounds," Ind. Eng. Chem. Res. 1997, 36, 1779-1790.*

* cited by examiner

*Primary Examiner*—Timothy C Vanoy
*Assistant Examiner*—Daniel Berns
(74) *Attorney, Agent, or Firm*—St. Onge Steward Johnston & Reens LLC

(57) ABSTRACT

Disclosed is an absorbent for separation of carbon dioxide from mixed gases, comprising a mixture of i) a compound of the chemical formula 1 having one or more groups of three functional groups consisting of amino group attached to a tertiary carbon atom; carboxylate group; and hydroxyl group respectively, in a molecule, or a compound of the chemical formula 2 having one or more groups of two functional groups consisting of amino group attached to a quarternary carbon atom; and carboxylate group respectively in a molecule, and ii) an amine compound which promotes the reaction.

The absorbent for separation of carbon dioxide of the present invention is advantageous economically, since its efficiency is excellent due to larger unit absorption amount of carbon dioxide, and the energy required for regeneration can be reduced due to the relatively wider difference of absorption amounts with temperature. In addition, it is advantageous for industrialization, since the solubility is excellent by using a compound presented as a form of carboxylic acid salts, and operation cost is low because there is no risk of evaporation due to high boiling point.

9 Claims, 3 Drawing Sheets

ABSORBENT FOR SEPARATION OF CARBON DIOXIDE

CROSS-REFERENCE TO RELATED APPLICATIONS

This application claims the priority of Korean Patent Applications No. 10-2006-0119336 filed on Nov. 29, 2006 in the Korean Intellectual Property Office, the disclosure of which is incorporated herein in its entirety by reference.

FIELD OF THE INVENTION

The present invention relates to an absorbent for the separation of carbon dioxide from mixed gases, comprising a mixture of i) a compound of the chemical formula 1 having one or more of amino group attached to tertiary carbon; carboxylate group; and hydroxyl group atom respectively in a molecule, or a compound of the chemical formula 2 having one or more of amino group attached to quaternary carbon atom; and carboxylate group respectively, in a molecule, and ii) an amine compound which promotes the reaction.

BACKGROUND OF THE INVENTION

There is a problem of global warming due to the increase of concentration of carbon dioxide in atmospheric air with industrial development. The main reason for the increase of concentration of carbon dioxide in the air is the use of fossil fuels such as coal, petroleum and LNG used in the energy industry.

The concentration of acid gases such as $CO_2$, $CH_4$, $H_2S$, COS and so on in the atmospheric air had been increased from the early 19th century when industrialization begins, and has been dramatically increased since the mid-twenty century. Regulations on the emission and treatment of these acid gases have been strict, as global warming due to the increase of concentration of the gases is accelerating. The international attention to global warming is rising during United Nations Conference on Environment and Development held at Rio, Brazil in June 1992. Industrialized countries including the United States and Japan have reached an agreement on reduction of acid gases, for example, they agreed to reduce emission amounts of green-house gases in 2010 by 5.2 percent compared with 1990. In particular, the separation of carbon dioxide which makes up 50 percent of acid gases that cause global warmed has become a more serious issue. Thus, the technological development for preparatory provision is urgently needed.

Techniques for controlling the increase of acid gases include, energy saving technique for less emission, separation and recovery technique of emitted acid gases, a technique that uses or fixes acid gases, alternative energy technique that emits acid gases, and so on. As acid gas separation techniques so far have studied, absorption, pressure swing adsorption, membrane filter method, and cryogenic distillation has been proposed as realistic alternatives.

In particular, the absorption method is easy to apply to most companies and energy plants since it is easy to treat huge amounts of gases and is suitable for separating low concentration of gases. For example, a process which use MEA (Monomethanolamine) manufactured by ABB Lummus Crest Co. as an absorbent is working at Trona, Calif., USA, and Shady Point, Okla., USA. However, the absorption process using MEA consumes much energy for separation of acid gases, uses a lot of absorption liquid, and causes a corrosion problem of separation equipment by the absorption liquid. Thus, the development of new additives and absorbents is urgently required.

Many researchers have studied the method for separation and recovery of acid gases such as $CO_2$, $CH_4$, $H_2S$, COS etc. from mixed gases emitted from smelters and Fossil Fuel Power Plants (Thermal power stations) by using the chemical reaction with an aqueous solution of alkanolamine. Conventional alkanolamines used widely include primary, secondary or tertiary amines such as monoethanolamine (MEA), diethanolamine (DEA), triethanolamine (TEA), N-methyl diethanolamine (MDEA), etc. Although MEA and DEA are especially used widely because of the advantage of high reaction velocity, it is known that there are lots of difficulties due to problems of high corrosiveness, high energy for recycling and degradation of these compounds. In addition, MDEA has a drawback of low reaction velocity, although its corrosiveness and energy for recycling are low.

Therefore, the development of a new absorbent is urgently required.

Recently, researches about sterically hindered amines as new alkanol amines absorbents are vigorously being carried out. The characteristic of such sterically hindered amines is that absorption capacity and selectivity for acid gas are high and the energy needed for recycling is low.

Primary and secondary amines generally go with the following reaction mechanism.

In case of tertiary amines such as MDEA and the like and sterically hindered amines, since the above reaction mechanism is unstable for the amines to follow, they go with the following reaction mechanism.

Accordingly, whereas two amines are required to absorb one carbon dioxide as primary and secondary amines used, tertiary amines and sterically hindered amines can provide double absorption capacity because carbon dioxide and amines react in molar ratio of 1:1.

The gas selectivity of such sterically hindered amines is very important factor in the present society in which regulations on the environment are strict, and their characteristic for recycling leads to save the energy and reduce total operational costs of acid gas treatment process.

Although the reaction velocity of sterically hindered amines depends on the extent of steric hindrance determined by the structure of amines, it is generally slower than reaction velocity of primary or secondary amines such as conventional MEA or DEA and the like, and faster than reaction velocity of tertiary amines. Sterically hindered amines about which recently many researches are being carried out include AMP and 2-piperidineethanol (PE).

In addition, the method of using amino acid salts as an absorbent with the chemical components which are different from that of conventional alkanol amines (Korean laid-open patent No. 2005-0007477, Jan. 18, 2005) is disclosed recently. In the above laid-open patent, potassium taurate used as absorbent causes accompanying environmental and economical problems to treat the precipitate generated by the reaction with carbon dioxide. Moreover, the potassium taurate has a disadvantage of requiring lots of energy in separation of carbon dioxide, since it is in a form of primary amino acid salts that do not have steric hindrance.

The present inventors have finally discovered an absorbent for separation of carbon oxide, which has a high carbon dioxide absorption capacity and does not need lots of energy for recycling.

The objective of the present invention is to provide an absorbent for separation of carbon oxide from mixed gases, having a high carbon dioxide absorption capacity, reducing energy for recycling, and having no disadvantages of the corrosiveness of equipments, etc.

SUMMARY OF THE INVENTION

In order to achieve the above objection, the present invention provides an absorbent for separation of carbon dioxide, comprising a mixture of i) a compound of the chemical formula 1 having one or more of amino group attached to tertiary carbon atom; carboxylate group; and hydroxyl group respectively, in a molecule, or a compound of the chemical formula 2 having one or more of amino group attached to quaternary carbon atom; and carboxylate group respectively, in a molecule, and ii) an amine compound which promotes the reaction:

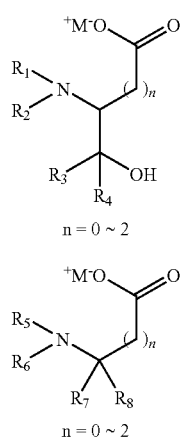

Chemical formula 1 n = 0 ~ 2

Chemical formula 2 n = 0 ~ 2 wherein $R_1$ to $R_8$ may be the same or different and each represents a hydrogen atom or a lower alkyl group of 1 to 4 carbon atoms, preferably a hydrogen atom or a lower alkyl group of 1 to 2 carbon atoms, and n is an integer of 0 to 2. Additionally, chemical formula 2 can only comprise a quarternary carbon atom if both $R_7$ and $R_8$ are carbon atoms, and neither are a hydrogen atom.

In the compound of the chemical formula 1, the number of each functional group of the amino group, carboxylate group and hydroxyl group are preferably contained in range of 1 to 5 in a molecule. If the number of each functional group is above 5, an absorption capacity of carbon dioxide is poor since their steric hindrance is large. If the number of each functional group is below 1, stripping ability of carbon dioxide is poor. The compound of the chemical formula 2 preferably contains amino group and carboxylate group in range of 1 to 5 respectably in a molecule. In this case, the hydroxyl group is useless because of the nucleophilicity and steric hindrance of amino group, increased by the substituents such as $R_7$ and $R_8$.

The examples of amino acid salts having the chemical formula 1 according to the present invention include, at least one compound selected from the group consisted of 3-(dimethylamino)-2-(hydroxyl) butyrate, 3-(dimethylamino)-2-(hydroxyl) pentanoate, 3-(methylamino)-2-(hydroxyl) butyrate, 3-(methylamino)-2-(hydroxyl) pentanoate, 3-(methylamino)-2-(hydroxyl)-2'-(methyl) butyrate, 3-(methylamino)-2-(hydroxyl)-2'-(methyl) pentanoate, 2-(methylamino)-1-(hydroxyl)-butyrate, 2-(methylamino)-1-(hydroxyl) propionate, serine, N-methylserine, N,N'-dimethylserine, and 2-(methylamino)-1-(hydroxyl)-1-(methyl)-serin.

The examples of the compound having the chemical formula 2 according to the present invention include, at least one compound selected from the group consisted of 2-(methyl)-2-(dimethylamino) butyrate, 2-(ethyl)-2-(dimethylamino) butyrate, 2-(methyl)-2-(methylamino) butyrate, 2-(ethyl)-2-(methylamino) butyrate, alpha-amino butyrate, 2-(methyl)-2-(dimethylamino) pentanoate, 2-(ethyl)-2-(dimethylamino) pentanoate, 2-(methyl)-2-(methylamino) pentanoate and 2-(ethyl)-2-(methylamino) pentanoate.

In addition, the carboxylic acid salts of the present invention are preferably the salts of alkali metal such as K, Na or Cs. Thus, the M of the chemical formula 1 and 2 may be alkali metal, preferably K, Na or Cs.

In the present invention, the concentration of an absorbent prepared by mixing a compound of the chemical formula 1 or 2 with amine compound is preferably in the range of 5~50% (w/v). If the concentration of the absorbent is below 5%, the absolute quantity of carbon dioxide absorbed is reduced due to low reaction velocity, although the carbon dioxide absorption capacity is maintained. If the concentration of the absorbent is above 50%, it is not efficient economically because of large amount of absorbent used although the absorption capacity and the absorbing velocity of carbon dioxide are excellent.

The absorbent according to the present invention comprises a mixture of the compound of the chemical formula 1 or the chemical formula 2 and the amine compound, wherein the amine compound does not only increase the velocity of absorption reaction of carbon dioxide but makes it easy to cause the stripping reaction at high temperature.

The examples of the amine compound according to the present invention include, at least one compound selected from the group consisted of 3,3'-diaminopropylamine, N-(2-aminomethyl)-1,3-propanediamine, piperazine, 2-aminomethylpiperazine, piperidine, morpholine, 4-piperidine methanol, 2,2'-(ethylenedioxy)-bis(ethylamine), monoethanolamine, 1,6-hexamethylenediamine, 4-aminomethylpiperidine, and 2-aminomethylpiperidine.

The amine compound used together with the amino acid salts of the chemical formula 1 or the chemical formula 2 is preferably added at a weight ratio of 1:0.1~5 to the amino acid salts of the chemical formula 1 or the chemical formula 2.

If the amine compound is added at a weight ratio below 0.1, it does not affect the reaction velocity. If the amine compound is added at a weight ratio above 5, the effect of increase of the reaction velocity compared with the amount of addition is not significant.

The hydroxyl group contained in the molecule of amino acid salts having the chemical formula 1 according to the present invention increases the concentration of the homogeneous solution since the hydroxyl group is soluble in itself to increase the solubility of the absorbent. Not only that, but the above-mentioned hydroxyl group also enhances the carbon dioxide absorption capacity of the absorbent since the nucleophilicity of amine located on the terminal of the absorbent increases due to electro-donating effect of the hydroxyl group.

In addition, there are tertiary and quaternary carbon atoms adjacent to the amine of amino acid salts having the chemical formula 1 or 2 according to the present invention. It is possible to reduce the amount of energy consumption in carbon dioxide stripping and recycling process for a removal of carbon dioxide after carbon dioxide absorption, due to the steric repulsion effect of the substituents group attached to the tertiary and quaternary carbon atoms.

The carboxylic acid salts in the molecule of the compound contained in the absorbent according to the present invention are soluble in itself to help to increase the solubility of the absorbent. In the present invention, salts of alkali metal, especially K, Na, or Cs as the carboxylic acid salts are preferably used, since they increase the solubility of amino acid salts.

According to one embodiment of the present invention, in order to prepare an absorbent containing a compound of the chemical formula 1 or 2, amino acid having amino group attached to tertiary or quaternary carbon atom respectively in the molecule is neutralized with a given amount of metal hydroxide, preferably alkali metal hydroxide at a slightly less level than the moles of the amino acid, to produce amino acid salts of the chemical formula 1 or 2. Specifically, amino acid having amino group attached to tertiary or quaternary carbon atom respectively in the molecule is added to deionized water at a weight ratio of 1:2~20, followed by dropping a 10~100% aqueous solution of metal hydroxide containing metal hydroxide at a molar ratio of 1:0.97~0.99 of the amino acid for 20~50 minutes, while dissolving in the thermostat maintained at 40~50° C. The mixture is then stirred for 12 or more hours to react sufficiently, thereby producing the amino acid salts of the chemical formula 1 or 2. After that, amine compound is added at a weight ratio of 1:0.1~5 to the said amino acid salt to obtain an 5~50% absorbent aqueous solution of the present invention containing a compound of the chemical formula 1 or 2.

The process for carbon dioxide absorption and separation comprises the steps of: absorbing carbon dioxide at low temperature; applying thermal energy at high temperature to separate the absorbed carbon dioxide from an absorbent; and feeding back the absorbent to the process. Thus, the step at which most of energy is spent in the process for carbon dioxide absorption and separation is a step of separating the absorbed carbon dioxide from an absorbent at high temperature to regenerate (strip) the absorbent. It is known that about 50~80% of energy of a total process is spent in this step. Therefore, the cost effectiveness of the process for separating carbon dioxide from an absorbent depends on how much energy can be reduced in an absorbent regenerating (stripping) step. That is, the absorbed carbon dioxide is preferably separated from the absorbent at low temperature.

An absorbent according to one embodiment of the present invention has a high absorption reaction with carbon dioxide at low temperature and a relatively poor absorption reaction at high temperature, so that the difference of carbon dioxide unit absorption amount by the temperature difference is very remarkable compared to conventional absorbents. It means that the absorbent according to the present invention can reduce energy required to separate carbon dioxide, that is, to regenerate the absorbent compared to conventional absorbents, for example, MEA. Namely, the absorbent and carbon dioxide do not react at high temperature, which means that the absorbent is easy to be regenerated so much. Accordingly, an entire carbon dioxide separation process using the absorbent can make sure the cost effectiveness.

DETAILED DESCRIPTION OF THE INVENTION

Examples

Figure 1:
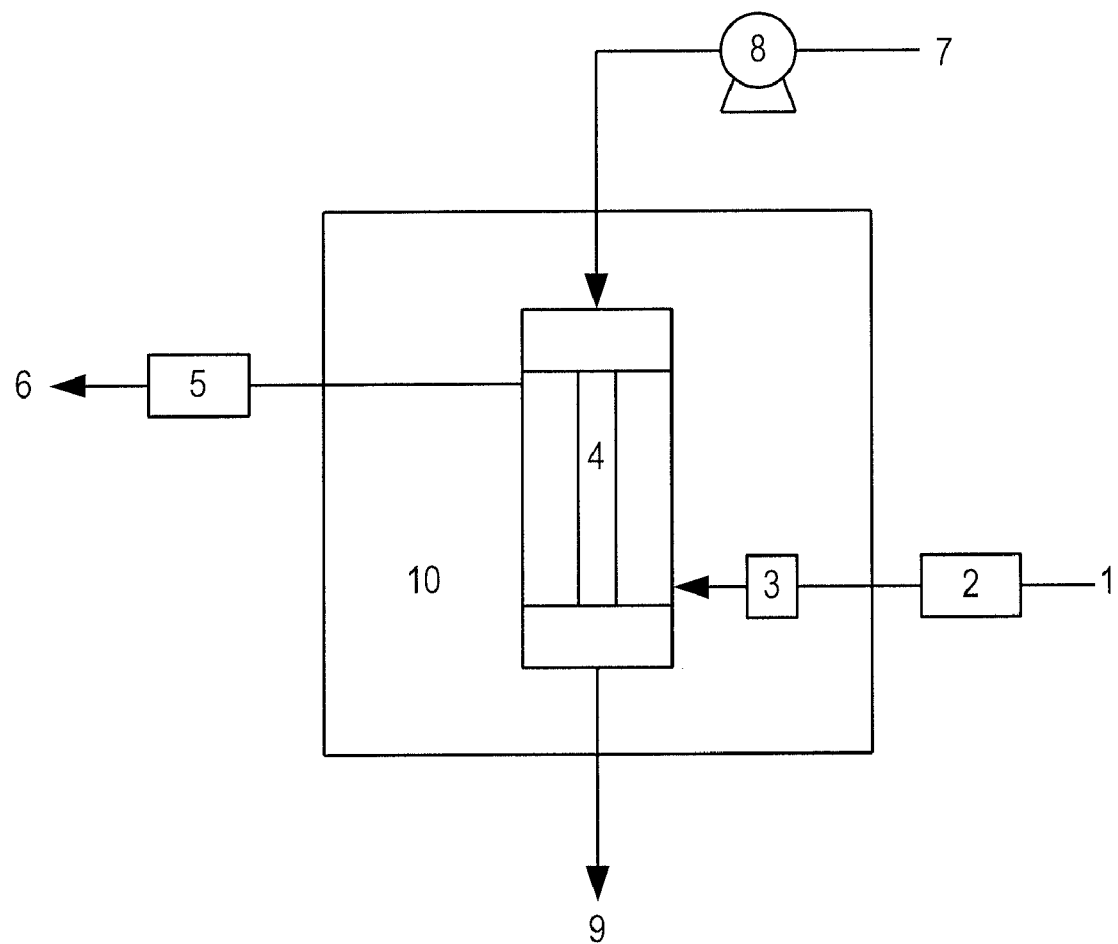
FIG. 1 is a schematic diagram illustrating an equipment for measuring the equilibrium absorption of carbon oxide according to the present invention.

This invention will be hereinafter described in more detail by way of examples. It is to be understood, however, that these examples are provided by way of illustration and nothing therein should be taken as a limitation upon the overall scope of the invention.

Preparation of an Absorbent:

Example 1

Preparation of a Compound of Chemical Formula 1

Serine (16.85 g: Sigma) was dissolved to deionized water (263.90 ml) in the thermostat maintained at 40~50° C., while dropping a KOH aqueous solution containing KOH at an amount of 0.01 mole less than that of serine for 30 minutes. The corresponding amino acid salt (serine salt) obtained thus was then stirred for 12 hours at a room temperature to react sufficiently.

Example 2

Preparation of a Compound of Chemical Formula 2

An alpha-aminobutyric acid salt was prepared according to the same manner as Example 1, except that an alpha-aminobutyric acid (Aldrich) in stead of serine is used.

Example 3

Preparation of an Absorbent Containing a Compound of Chemical Formula 1

Serine (16.85 g: Sigma) was dissolved to deionized water (263.90 ml) in the thermostat maintained at 40~50° C., followed by dropping a 45 wt % KOH aqueous solution (19.59 g) for 30 minutes. The mixture was then stirred at a room temperature for 12 or more hours to react sufficiently, followed by mixing piperazine (7.5 g) to prepare a 10% aqueous solution of an absorbent according to the present invention. (The weight ratio of serine salt:piperazine=3:1).

Example 4

Preparation of an Absorbent Containing a Compound of Chemical Formula 2

A 10% aqueous solution of an absorbent was prepared according to the same manner as Example 3, except that an alpha-aminobutyric acid (16.60 g) in stead of serine is used.

Example 5

A 10% aqueous solution of an absorbent was prepared according to the same manner as Example 3, except that serine (22.24 g) was dissolved to deionized water (252.33 ml), followed by dropping a 45 wt % KOH aqueous solution (25.86 g), and the mixture was then stirred at a room temperature for 12 or more hours to react sufficiently, followed by mixing piperazine (0.3 g). (The weight ratio of serine salt:piperazine=1:0.1).

Example 6

A 10% aqueous solution of an absorbent was prepared according to the same manner as Example 4, except that alpha-aminobutyric acid (21.91 g) was dissolved to deionized water (252.08 ml), followed by dropping a 45 wt % KOH aqueous solution (26.22 g) for 30 minutes. The mixture was then stirred at a room temperature for 12 or more hours to react sufficiently, followed by mixing piperazine (0.3 g) (The weight ratio of alpha-aminobutyric acid salt:piperazine=1:0.1).

Example 7

A 10% aqueous solution of an absorbent was prepared according to the same manner as Example 3, except that serine (3.74 g) was dissolved to deionized water (291.98 ml), followed by dropping a 45 wt % KOH aqueous solution (4.35 g) for 30 minutes, and the mixture was then stirred at a room temperature for 12 or more hours to react sufficiently, followed by mixing piperazine (25.25 g). (The weight ratio of serine salt:piperazine=1:5).

Example 8

A 10% aqueous solution of an absorbent was prepared according to the same manner as Example 4, except that alpha-aminobutyric acid (3.69 g) was dissolved to deionized water (291.93 ml), followed by dropping a 45 wt % KOH aqueous solution (4.41 g) for 30 minutes, and mixture was then stirred at a room temperature for 12 or more hours to react sufficiently, followed by mixing piperazine (25.25 g). (The weight ratio of alpha-aminobutyric acid salt:piperazine=1:5).

Example 9

A 30% aqueous solution of an absorbent was prepared according to the same manner as Example 3, except that serine (50.55 g) was dissolved to deionized water (191.68 ml), followed by dropping a 45 wt % KOH aqueous solution (58.78 g) for 30 minutes, and the mixture was then stirred at a room temperature for 12 or more hours to react sufficiently, followed by mixing piperazine (22.5 g). (The weight ratio of serine salt:piperazine=3:1).

Example 10

A 30% aqueous solution of an absorbent was prepared according to the same manner as Example 4, except that alpha-aminobutyric acid (49.79 g) was dissolved to deionized water (191.10 ml), followed by dropping a 45 wt % KOH aqueous solution (59.60 g) for 30 minutes, and the mixture was then stirred at a room temperature for 12 or more hours to react sufficiently, followed by mixing piperazine (22.5 g). (The weight ratio of alpha-aminobutyric acid salt:piperazine=3:1).

Test Example 1

Preparation of an Equipment for Comparison of Carbon Dioxide Unit Absorption Amount FIG. 1 illustrates schematically equipment for measuring equilibrium $CO_2$ absorption capacity of absorbents under an atmosphere pressure. The above equipment is consisted of: a storage reservoir 3 through which the exact amount of carbon dioxide can be injected at a certain temperature; and a reactor tank 4 in which carbon dioxide and an absorbent can react at a certain temperature. The storage reservoir and reactor tank was installed in Forced Convection Oven (OF-22) 10 manufactured by JEIOTECH Co., LTD., so as to maintain a certain temperature. An absorbent was injected at an exact amount through a pump 8 (Series 1; Lab Alliance Co.), and 4 baffles was installed in the reactor tank for a smooth reaction so that a homogeneous mixture was attained. Thermometers were installed at a gas phase and a liquid phase side both, and a manometer was equipped at a gas phase side. The thermometer and the manometer were connected to the Hybrid Recorder (DR-230) so that their numerical values were stored as data files by way of the transmission of computers.

In order to measure the equilibrium $CO_2$ absorption capacity of an absorbent, the storage reservoir was charged with a given amount of carbon dioxide introduced through a gas pressure regulator 2 from a gas inlet 1, and the reactor tank was maintained at the state of pure nitrogen without carbon dioxide. After that, the reactor tank 3 was sufficiently purged away with nitrogen gas until carbon dioxide was not detected when analyzed by a gas chromatography (GC) after discharging a predetermined amount of gas to a gas outlet 6 through gas flow meter 5. About 100 g of absorbent was then injected into the reactor tank from a absorbent inlet 7 by using the pump 8 (Series 1), and the temperature of the oven was set to the temperature at which the measurement was stared, to measure an equilibrium pressure at the corresponding temperature. This equilibrium pressure is a basic pressure of nitrogen gas and the absorbent. When the temperature reached each temperature of the measurement object, the valve of carbon dioxide storage reservoir was opened so that carbon dioxide was provided into the reactor tank. After that, when the equilibrium pressure and temperature of the carbon dioxide reactor tank became certain, it was judged that the reaction was finished. At this point, changes of the pressure of the carbon dioxide reactor tank and carbon dioxide storage reservoir were measured to estimate the solubility by calculating the partial pressure using the equilibrium load and the gas amount of flowed carbon dioxide. The absorbent of which the reaction for regeneration is completed is discharged out through an absorbent outlet 9.

Comparison of carbon dioxide unit absorption amount by temperature difference between MEA and an absorbent according to Example 3

Test Example 2

Comparison Between MEA and an Absorbent According to Example 3

As a comparative example, the test was carried out for comparison of the difference of carbon dioxide unit absorption amount with temperature for a 10 wt % aqueous solution of monoethanolamine (MEA) which is widely used as carbon dioxide absorbent conventionally and an absorbent according to Example 3, at 35° C., 100° C., and 125° C. respectively.

Figure 2:
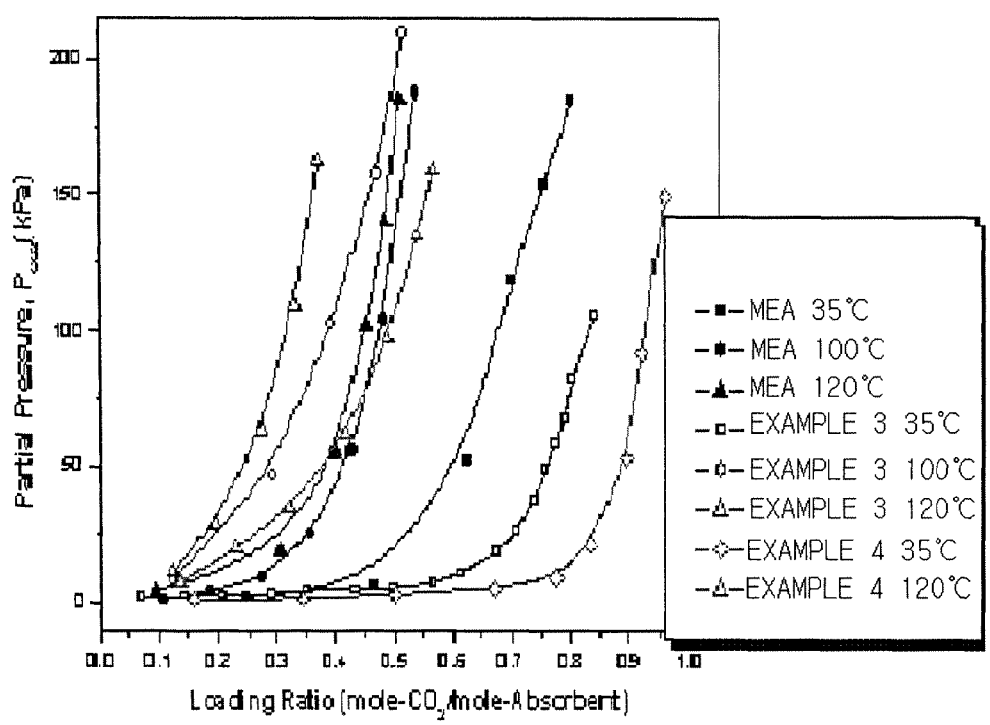
FIG. 2 is a graph showing the changes of carbon dioxide absorption capacity and stripping performance with temperature of an absorbent according to the present invention and MEA.

The data which has shown the comparison of the test results, is given in Table 1 below, and the corresponding graph is shown in FIG. 2.

been carried out at 100° C.~120° C., and in this case, when MEA is used, the absorption reaction of carbon dioxide and MEA is vigorously advanced at 120° C. as well as at 100° C.

TABLE 1

| comparative example MEA (35° C.) | | comparative example MEA (100° C.) | | comparative example MEA (120° C.) | | Example 3 absorbent (35° C.) | | Example 3 absorbent (100° C.) | | Example 3 absorbent (120° C.) | |
|---|---|---|---|---|---|---|---|---|---|---|---|
| absorption (mole-$CO_2$/ mole-MEA) | partial pressure (Pco2, kPa) | absorption (mole-$CO_2$/ mole-MEA) | partial pressure (Pco2, kPa) | absorption (mole-$CO_2$/ mole-MEA) | partial pressure (Pco2, kPa) | absorption (mole-$CO_2$/ mole-amine) | partial pressure (Pco2, kPa) | absorption (mole-$CO_2$/ mole-amine) | partial pressure (Pco2, kPa) | absorption (mole-$CO_2$/ mole-amine) | partial pressure (Pco2, kPa) |
| 0.2451 | 2.2741 | 0.1065 | 1.3782 | 0.0940 | 4.1347 | 0.0740 | 2.0673 | 0.1248 | 8.9585 | 0.1232 | 11.715 |
| 0.4647 | 6.2710 | 0.1861 | 4.1347 | 0.3072 | 19.2952 | 0.5667 | 7.5803 | 0.2949 | 46.8599 | 0.1957 | 28.9429 |
| 0.6235 | 52.1661 | 0.2763 | 9.6476 | 0.4007 | 55.1293 | 0.7383 | 37.9014 | 0.3956 | 102.6782 | 0.2735 | 69.3986 |
| 0.6995 | 118.6557 | 0.3587 | 24.8082 | 0.4537 | 101.989 | 0.7741 | 58.5748 | 0.4717 | 157.11184 | 0.3323 | 109.5694 |
| 0.7565 | 153.397 | 0.4282 | 55.8184 | 0.4872 | 140.5796 | 0.8033 | 82.6938 | 0.5181 | 209.4912 | 0.3726 | 161.9422 |
| 0.8014 | 184.6830 | 0.4836 | 104.0565 | 0.5109 | 185.3721 | 0.8416 | 105.4347 | | | | |
| | | 0.5362 | 187.4395 | | | | | | | | |

Test Example 3

Comparison Between MEA and an Absorbent According to Example 4

The test was carried out according to the same manner as Test example 2, except that the absorbent solution of Example 4 in stead of the absorbent solution of Example 3 is used. The test result is shown in Table 2 below and is illustrated in FIG. 2.

This result implies that absorbed carbon dioxide is not vigorously separated (stripped) from the MEA at 100° C., and that the amount of carbon dioxide absorbed while separating (stripping) from the conventional absorbent (MEA) is considerable even at 120° C. Therefore, it can be seen that in case of MEA, the conventional absorbent, high temperature of 120° C. or more is required for stripping of carbon dioxide, and accordingly a good deal of energy is essentially needed.

TABLE 2

| comparative example MEA (35° C.) | | comparative example MEA (100° C.) | | comparative example MEA (120° C.) | | Example 4 absorbent (100° C.) | | Example 4 absorbent (120° C.) | |
|---|---|---|---|---|---|---|---|---|---|
| absorption (mole-$CO_2$/ mole-MEA) | partial pressure (Pco2, kPa) | absorption (mole-$CO_2$/ mole-MEA) | partial pressure (Pco2, kPa) | absorption (mole-$CO_2$/ mole-MEA) | partial pressure (Pco2, kPa) | absorption (mole-$CO_2$/ mole-amine) | partial pressure (Pco2, kPa) | absorption (mole-$CO_2$/ mole-amine) | partial pressure (Pco2, kPa) |
| 0.2451 | 2.2741 | 0.1065 | 1.3782 | 0.0940 | 4.1347 | 0.1604 | 1.3782 | 0.1376 | 8.2694 |
| 0.4641 | 6.2710 | 0.1861 | 4.1347 | 0.3072 | 19.2952 | 0.5028 | 3.4456 | 0.2332 | 19.9844 |
| 0.6235 | 52.1661 | 0.2763 | 9.6476 | 0.4007 | 55.1293 | 0.7760 | 9.6476 | 0.3228 | 35.1449 |
| 0.6995 | 118.6557 | 0.3587 | 24.8082 | 0.4537 | 101.9891 | 0.8345 | 21.3626 | 0.4185 | 62.0204 |
| 0.7565 | 153.3971 | 0.4282 | 55.8184 | 0.4872 | 140.5796 | 0.8944 | 53.0619 | 0.4907 | 97.1653 |
| 0.8014 | 184.6830 | 0.4836 | 104.0565 | 0.5109 | 185.3721 | 0.9205 | 91.6524 | 0.5400 | 135.0667 |
| | | 0.5362 | 187.4395 | | | 0.9595 | 149.5381 | 0.5690 | 159.1857 |

As can be seen from the result of Comparative Examples and Examples above, the absorbent for separation of carbon dioxide according to the present invention has a wide difference of carbon dioxide unit absorption amount by temperature difference compared to MEA. That is, the absorbent according to the present invention has a large unit absorption amount at low temperature, and has a small unit absorption amount at high temperature compared to MEA. It can be seen from this result that when the absorbent according to the present invention separates carbon dioxide, less energy is required compared to MEA.

FIG. 2 is a graph showing the test result obtained from Table 1 and Table 2. It can be seen from FIG. 2 that the conventional carbon oxide separation and regeneration (stripping) process using MEA which is well-known till now has It can be made sure from this, that there is a problem of economical efficiency of the process.

However, the absorbent according to the present invention, as representing the curve in which carbon dioxide is shown not to be nearly absorbed at 100° C., can strip carbon dioxide at low temperature compared to MEA. In comparison, it has a wide difference of absorption capacity with temperature due to relatively high absorption capacity at low temperature, thereby reducing considerably energy (about 50~80% of an entire process) consumed for stripping carbon dioxide. Therefore, it can be seen that the absorbent of the present invention is advantageous for economical efficiency and practicality (industrialization).

Comparison of the Reaction Velocity with Carbon Dioxide

Test Example 4

Figure 3:
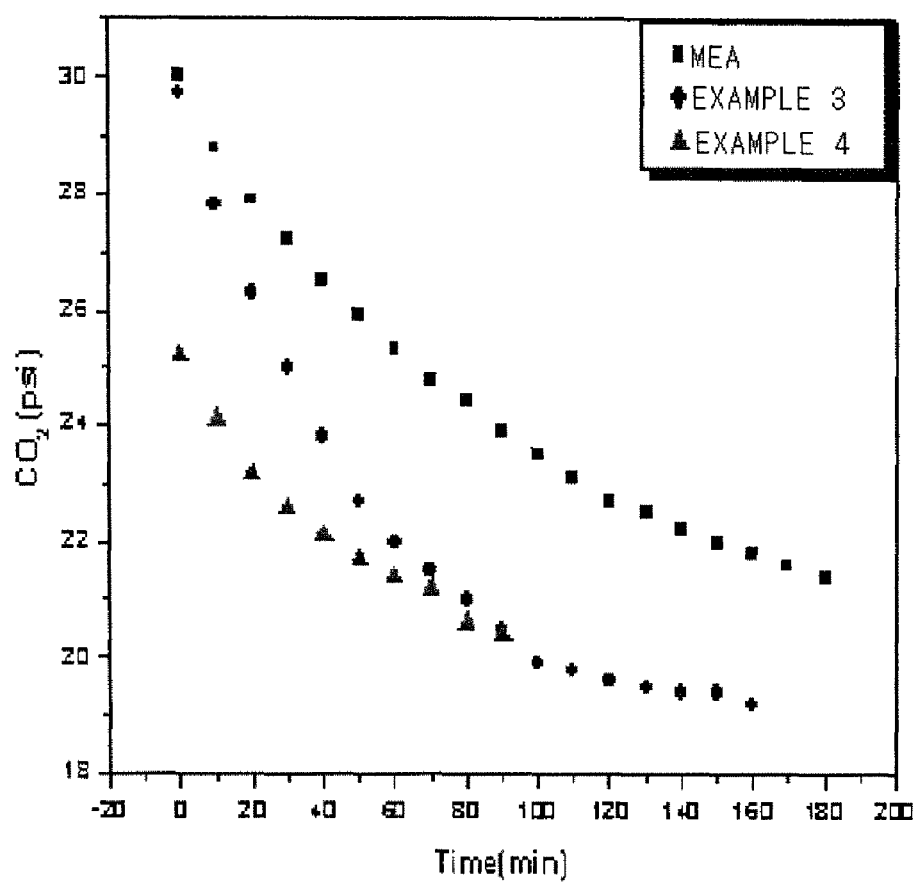
FIG. 3 is a graph showing reaction velocity of an absorbent according to an embodiment of the present invention and MEA at 35° C.

In order to compare the reaction velocity with carbon dioxide of the absorbent of Example 3 with that of the absorbent of Comparative Example at the condition of carbon dioxide absorption (35° C.), a partial pressure of carbon dioxide in the storage reservoir is measured by using the equipment of Test Example 1, and this result is shown in FIG. 3. FIG. 3 illustrates the partial pressure (the concentration) of carbon dioxide with time, which means that the sooner the partial pressure reduces, the higher the reaction velocity is. As shown in FIG. 3, since in case of the absorbent of Example 3, as we know from the result that the amount of carbon dioxide reduced is large for the same hours compared to MEA, the absorption reaction is advanced rapidly, so that reaction velocity is high. In addition, in case of the absorbent of Example 4, a slope of the curve showing that the partial pressure of carbon dioxide decreases is similar to the absorbent of Comparative Examples, which means excellent, as shown in FIG. 3. Therefore, the difference of unit absorption amount of carbon dioxide by temperature difference is exceptionally wide, compared to Comparative Examples, as shown in FIG. 2. Therefore, it can be seen that an absorbent according to the present invention needs less energy in separation of carbon dioxide compared to MEA, since the capacity absorption of carbon dioxide by temperature difference is excellent while the velocity of the reaction that absorbs carbon dioxide is similar to that of Comparative Examples.

As above-mentioned in detail, the absorbent for separation of carbon dioxide of the present invention is advantageous economically, since its efficiency is excellent due to large unit absorption amount of carbon dioxide, and the thermal energy required for regeneration (recycling) can be reduced due to wide difference of absorption amount with temperature, compared to absorbents used conventionally. In addition, it is advantageous for industrialization, since its solubility is excellent by using a compound presented as a form of carboxylic acid salts together with amine compounds, and operational cost is low as there is no risk of evaporation due to high boiling point.

What is claimed is:

1. An absorbent for the separation of carbon dioxide from mixed gases, comprising a mixture of i) a compound of the chemical formula 1 having one or more of each of amino group attached to tertiary carbon atom; carboxylate group; and hydroxyl group as functional groups, in a molecule and ii) an amine compound which promotes the reaction

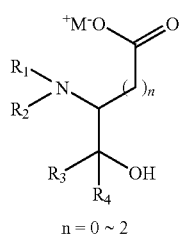

Chemical formula 1

$n = 0 \sim 2$ wherein $R_1$ to $R_4$ may be the same or different and each represents a hydrogen atom or a lower alkyl group of 1 to 4 carbon atoms and n is an integer of 0 to 2, and M is alkali metal.

2. The absorbent for the separation of carbon dioxide of claim 1, wherein the compound of chemical formula 1 contains each of the amino group, carboxylate group and hydroxyl group as functional groups in range of 1 to 5 in a molecule.

3. The absorbent for the separation of carbon dioxide of claim 1, wherein M of the chemical formula 1 is K, Na or Cs.

4. The absorbent for the separation of carbon dioxide of claim 1, wherein the absorbent is used as an aqueous solution in the range of 5~50% (w/v).

5. The absorbent for the separation of carbon dioxide of claim 1, wherein the amine compound is added at a weight ratio of 1:0.1~5 to the amino acid salts of the chemical formula 1.

6. The absorbent for the separation of carbon dioxide of claim 3, wherein the compound of the chemical formula 1 include a mixture of one or more selected from the group consisting of 3-(dimethylamino)-2-(hydroxyl)-butyrate, 3-(dimethylamino)-2-(hydroxyl)-pentanoate, 3-(methylamino)-2-(hydroxyl)-butyrate, 3-(methylamino)-2-(hydroxyl)-pentanoate, 3-(methylamino)-2-(hydroxyl)-2'-(methyl)-butyrate, 3-(methylamino)-2-(hydroxyl)-2'-(methyl)-pentanoate, 2-(methylamino)-1-(hydroxyl)-butyrate, 2-(methylamino)-1-(hydroxyl)-propionate, serine, N-methylserine, N,N'-dimethylserine, and 2-(methylamino)-1-(hydroxyl)-1-(methyl)-serin.

7. The absorbent for the separation of carbon dioxide of claim 1, wherein the amine compound includes a mixture of one or more selected from the group consisting of 3,3'-diaminopropylamine, N-(2-aminomethyl)-1,3-propanediamine, piperazine, 2-aminomethylpiperazine, piperidine, morpholine, 4-piperidine methanol, 2,2'-(ethylenedioxy)-bis(ethylamine), monoethanolamine, 1,6-hexamethylenediamine, 4-aminomethylpiperidine, and 2-aminomethylpiperidine.

8. The absorbent for the separation of carbon dioxide of claim 1, wherein $R_1$ to $R_8$ may be the same or different and each represents a hydrogen atom or a lower alkyl group of 1 to 2 carbon atoms.

9. An absorbent for the separation of carbon dioxide from mixed gases, comprising a mixture of i) a compound of the chemical formula 2 having one or more of each of amino group attached to quaternary carbon atom; and carboxylate group as functional groups, in a molecule, and ii) an amine compound which promotes the reaction

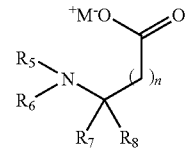

Chemical formula 2

$n = 0 \sim 2$ wherein $R_5$ and $R_6$ may be the same or different and each represents a hydrogen atom or a lower alkyl group of 1 to 4 carbon atoms, $R_7$ and $R_8$ may be the same or different and each represents a lower alkyl group of 1 to 4 carbon atoms, and n is an integer of 0 to 2, and M is alkali metal, and wherein the compound of the chemical formula 2 includes a mixture of one or more selected from the group consisting of 2-(methyl)-2-(dimethylamino)-butyrate, 2-(ethyl)-2-(dimethylamino)-butyrate, 2-(methyl)-2-(methylamino)-butyrate, 2-(ethyl)-2-(methylamino)-butyrate, alpha-amino butyrate, 2-(methyl)-2-(dimethylamino)-pentanoate, 2-(ethyl)-2-(dimethylamino)-pentanoate, 2-(methyl)-2-(methylamino)-pentanoate and 2-(ethyl)-2-(methylamino) pentanoate.

* * * * *